United States Patent
Kana et al.

(10) Patent No.: US 10,166,115 B2
(45) Date of Patent: Jan. 1, 2019

(54) INTERBODY FUSION DEVICE

(71) Applicant: SpineSmith Partners, L.P., Austin, TX (US)

(72) Inventors: Richard J. Kana, Lexington, TX (US); Kevin Dunworth, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 127 days.

(21) Appl. No.: 14/055,736

(22) Filed: Oct. 16, 2013

(65) Prior Publication Data

US 2014/0046448 A1     Feb. 13, 2014

Related U.S. Application Data

(63) Continuation-in-part of application No. 14/020,374, filed on Sep. 6, 2013, and a continuation-in-part of application No. 13/135,675, filed on Jul. 12, 2011, and a continuation-in-part of application No. 13/200,911, filed on Oct. 4, 2011, now Pat. No. 8,597,353.

(60) Provisional application No. 61/714,385, filed on Oct. 16, 2012.

(51) Int. Cl.
    *A61F 2/44*     (2006.01)
    *A61F 2/30*     (2006.01)

(52) U.S. Cl.
    CPC .......... *A61F 2/447* (2013.01); *A61F 2/30744* (2013.01); *A61F 2/4455* (2013.01); *A61F 2/4465* (2013.01); *A61F 2002/3008* (2013.01); *A61F 2002/3023* (2013.01); *A61F 2002/30787* (2013.01); *A61F 2002/30904* (2013.01); *A61F 2002/4475* (2013.01)

(58) Field of Classification Search
    CPC .............................. A61F 2/447; A61F 2/4465
    See application file for complete search history.

(56) References Cited

U.S. PATENT DOCUMENTS

| | | | | |
|---|---|---|---|---|
| 6,482,233 | B1 * | 11/2002 | Aebi ..................... | A61F 2/4465 623/17.11 |
| 7,172,627 | B2 * | 2/2007 | Fiere .................. | A61B 17/7059 623/17.11 |
| 2005/0004671 | A1 * | 1/2005 | Ross ................... | A61F 2/30744 623/17.11 |
| 2005/0085913 | A1 * | 4/2005 | Fraser ................ | A61B 17/7059 623/17.11 |
| 2008/0306596 | A1 * | 12/2008 | Jones ................... | A61F 2/4455 623/17.16 |
| 2009/0105831 | A1 * | 4/2009 | Jones ................. | A61B 17/7059 623/17.16 |
| 2010/0057206 | A1 * | 3/2010 | Duffield et al. ............ | 623/17.16 |
| 2010/0106249 | A1 * | 4/2010 | Tyber ..................... | A61F 2/447 623/17.11 |

* cited by examiner

*Primary Examiner* — Olivia C Chang
(74) *Attorney, Agent, or Firm* — Winstead PC

(57) ABSTRACT

The invention is directed to an interbody fusion device comprises a fusion bearing device and a retention device and further comprises two bone screws that pass through the retention device and into the vertebral bodies. When implanted, the construct is flush with the anterior face of the vertebras and provides support and temporary fixation for the ultimate fusion of the vertebral bodies.

20 Claims, 2 Drawing Sheets

INTERBODY FUSION DEVICE

CROSS-REFERENCES TO RELATED APPLICATIONS

This Application claims the benefit under 35 U.S.C. § 119(e) of U.S. Provisional Patent Application No. 61/714,385 filed Oct. 16, 2012, which is incorporated herein by reference in its entirety as if fully set forth herein. This Application is a continuation-in-part of application Ser. No. 13/135,675 filed Jul. 12, 2011, and is a continuation-in-part of application Ser. No. 13/200,911 filed Oct. 4, 2011, and is a continuation-in-part of application Ser. No. 14/020,374 filed Sep. 6, 2013, each of which is incorporated herein by reference in its entirety as if fully set forth herein.

BACKGROUND OF THE INVENTION

The spine is a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

There is a need for spinal fusion devices and instruments, as well as related spinal fusion procedures, that adequately treats degenerative disc disease and other spinal conditions, while providing improvements over the prior art.

SUMMARY OF THE INVENTION

An embodiment of the invention provides a fusion bearing device that is substantially rectangular shaped and is configured to fit between two adjacent vertebrae, the fusion bearing device having one or more openings to allow access to the end plates of the two adjacent vertebrae, a retention device configured to prevent migration of the fusion bearing device, and one or more fasteners coupled to the retention device to compress the two adjacent vertebrae to the fusion bearing device.

In one embodiment, a spinal fusion device, including a fusion bearing device, is configured to fit between two adjacent vertebrae, the fusion bearing device having an open end, and a retention device configured to couple to the fusion bearing device, at least partially closing the open end.

DETAILED DESCRIPTION OF EXEMPLARY EMBODIMENTS

In an embodiment of the invention, the interbody fusion device comprises a fusion bearing device and a retention device and further comprises two bone screws that pass through the retention device and into the vertebral bodies. When implanted, the construct is flush with the anterior face of the vertebras and provides support and temporary fixation for the ultimate fusion of the vertebral bodies.

The present invention relates to spinal fusion implants and related spinal fusion procedures for use in cervical and lumbar applications. One type of spinal fusion is interbody fusion. Typically, an interbody fusion procedure places a bone graft between the vertebrae in the area normally occupied by an intervertebral disc. In preparation for a spinal fusion procedure, the intervertebral disc is removed. A device, typically containing a bone promoting matrix, such as allograph bone, may be placed between the vertebra to maintain spine alignment and disc height. Fusion then occurs between the endplates of the vertebrae. In some examples, fusion is augmented by a process called fixation, meaning the placement of screws, rods and/or plates to stabilize the vertebra to facilitate bone fusion. The present invention provides an interbody fusion device that overcomes problems found in the prior art, such as the angles of the screws, rods and/or plates that are used to stablize the vertebra.

Generally, the present invention provides a two piece interbody fusion device that may be used to perform anterior lumbar interbody fusion (ALIF). In one example, a first piece of the interbody fusion device is a ring-shaped load bearing device that is designed to bear the axial loading from the end plates of adjacent vertebrae. A second piece of the interbody fusion device is a retention component, which may be attached to the ring-shaped load bearing device, whose function is to prevent migration of the load bearing device and to prevent loss or migration of the bone forming matrix placed therein. One or more fasteners, such as bone screws secure the retention component to the vertebrae above and below the load bearing device. The fasteners cause the end plates of the vertebrae to compress the end plates to the load bearing device to facilitate proper fusion. If desired, the fasteners may include an anti backout mechanism to prevent their migration.

Figure 1:
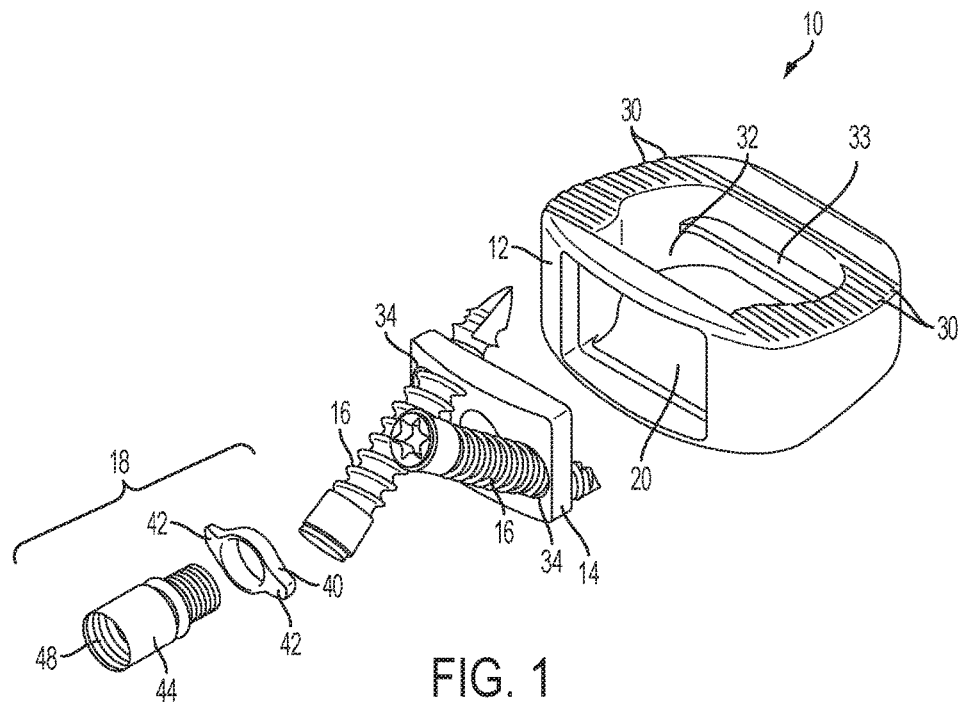
FIG. 1 is an exploded diagram of the interbody fusion device shown in accordance with an embodiment of the invention.

FIG. 1 is an isometric view of one example of an interbody fusion device of the present invention. FIG. 1 shows an interbody fusion device 10. The interbody fusion device 10 includes a load bearing device 12, a retention component 14, two bone screws 16, and an anti-backout mechanism 18, each of which are described in more detail below. The interbody fusion device comprises a hollow region 32 which can be filled with a prepared material such as a bone forming matrix to help facilitate fusion of the vertebrae.

In an embodiment of the invention, the height of the retention component 14 is less than the height of the load bearing device 12. This feature allows the retention component 14 to be put in place without interfering with the relative placement of the load bearing device 12 and the end plates of the adjacent vertebrae.

FIG. 1 also illustrates the components of the anti backout mechanism 18. The anti backout mechanism 18 includes a locking plate 40. The plate 40 has two opposing protrusions 42 that extend outward from the plate 40. A set screw 44 is configured to extend through an opening formed in the plate 40, and thread into the retention component 14. The set screw 44 includes a head 48 that will shear off when enough torque is applied by a driver. By shearing off the head 48, the surgeon will know that the set screw 44 is tight enough, and it will reduce the profile of the fusion device 10. The retention component 14, locking plate 40, and set screw 44 can be pre assembled, such that a surgeon will have a single piece that is attached to the load bearing device 12. Once the bone screws are installed, the surgeon needs only to turn the set screw 44 with a driver to lock the bone screws in place. When the head 48 shears off, it will stay attached to the driver as the surgeon removes the driver from the patient. The set screw in this example includes a driver socket for receiving a driver, which may be used by a surgeon to tighten the set screw 44. The implant construct thus maintains a zero profile to the anterior vertebral face.

Figure 2A:
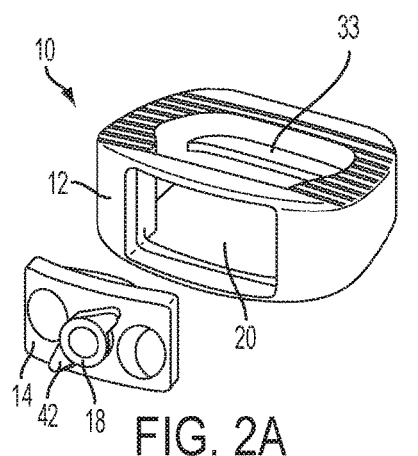
FIG. 2A and FIG. 2B are exploded diagrams of the interbody fusion device shown in FIG. 1 without the bone screws in accordance with an embodiment of the invention.
Figure 2B:
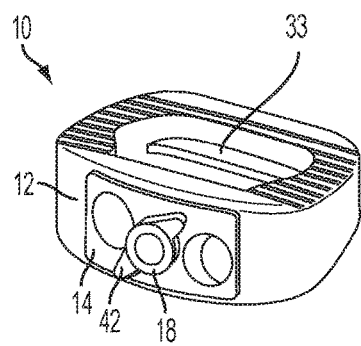

FIG. 2A is an exploded view of the interbody fusion device 10, showing the load bearing device 12, the retention component 14, and the anti backout mechanism 18 separately. The load bearing device 12 is a generally ring-shaped device. The front portion edge of the load bearing device 12 contains a window 20 that is capable of accepting the plate-like retention component 14. The window 20 allows in-situ vertebral face preparation along with in-situ graft delivery. FIG. 2B shows the interbody fusion device 10 wherein the retention component 14 is placed in the window 20.

The load bearing device 12 also includes a plurality of ridges 30 formed on the top and bottom ends of the device 12 and a shelf 33 that extends away from an inner wall of the load bearing device 12 into the hollow region 32. The ridges 30 are angled and pointed in such a way that the ridges 30 help to hold the load bearing device 12 to the end plates of the vertebrae to reduce the chance of anterior migration of the implant. If desired, one or more openings (not shown) can be formed in the load bearing device 12 to facilitate the attachment of instrumentation devices. The shelf 33 is disposed on the inner wall of the load bearing device 12 on a side of the load bearing device 12 opposite the window 20. The shelf 33 comprises a planar, shelf-like portion that extends across a width of the load bearing device 12. As shown in FIGS. 1, 2A, and 2B, the shelf 33 is disposed on the inner wall of the load bearing device 12 such that a portion of the inner wall is disposed both above and below the shelf 33.

Figure 3A:
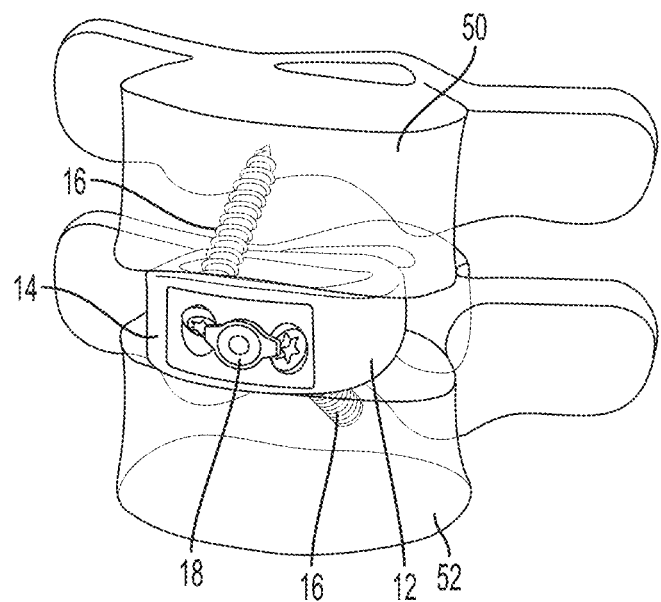
FIG. 3A and FIG. 3B are diagrams of the interbody fusion device shown in FIG. 1 installed between the end plates of two adjacent vertebrae.
Figure 3B:
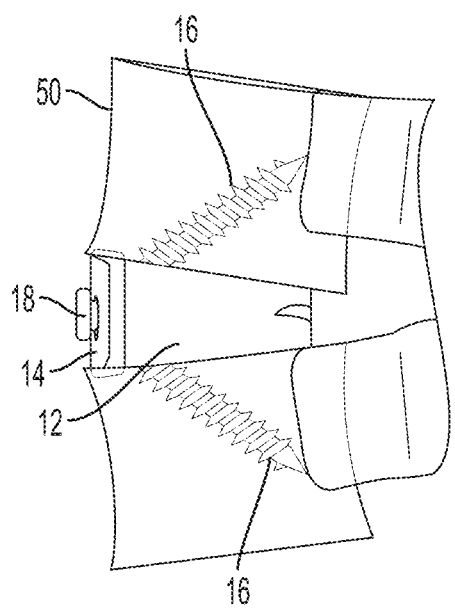

As described above, an interbody fusion device of the present invention is intended to be installed between the end plates of two adjacent vertebrae to facilitate the fusion of the vertebrae. FIG. 3A is an isometric diagram of the interbody fusion device 10 shown in FIG. 1 installed between the end plates of two adjacent vertebrae 50 and 52 to facilitate the fusion of the vertebrae 50 and 52. FIG. 3B shows a side view of the interbody fusion device 10 shown in FIG. 1 installed between the end plates of two adjacent vertebrae 50 and 52. The interbody fusion device 10 provides load bearing support as well as the proper spacing between the vertebrae 50 and 52 while fusion of the vertebrae takes place. As described in more detail below, the interbody fusion device 10 is positioned between the end plates of the vertebrae 50 and 52 within the vertebral body in the area usually occupied by the intervertebral disc. For clarity, the disc annulus is not shown, so the position of the load supporting device 12 can be seen.

Following is an example of how an interbody fusion device of the present invention may be used in an ALIF spinal fusion procedure. As described above, a window is cut in the anterior side of the disc annulus to allow an interbody fusion device to be inserted. Next, the nucleus pulpous is cleaned out to provide room for the interbody fusion device. Next, a load bearing device 12 of the desired size (e.g., having a height to get the desired spacing between the vertebrae and surface area to maximize coverage of the endplates) is inserted between the end plates of the adjacent vertebrae using the appropriate instrumentation. Once the surgeon is satisfied that the load bearing device is in the desired position, the end plates can be prepared using the appropriate instruments (e.g., burrs, gouges, curettes, etc.). Next, the space between the endplates and within the load bearing device can be filled with a material that will help to facilitate fusion. Next, the retention component 14 is coupled to the load bearing device 12. Note that, because the height of the retention component is less than the height of the load bearing device, the retention component 14 can be put in place without interfering with the relative placement of the load bearing device 12 and the end plates of the adjacent vertebrae. Also, the retention component 14 is stress shielded and is not axial loaded by the vertebrae. Once the retention component is in place, the bone screws 16 can be installed through the openings 34 and into the vertebrae. As the bone screws 16 are tightened, the vertebrae will compress vertebral bodies 50 and 52 onto the load bearing member 12, which will help facilitate fusion. Also, since the bone screws 16 secure the retention component 14, and do not directly secure the load bearing device 12, the bone screws will not tend to cause the interbody fusion device 10 to migrate. Next, the anti backout mechanism 18 is engaged to prevent the bone screws 16 from loosening. As is described in detail below, the surgeon can turn the set screw 44 with driver until the head 48 sheers off. The protrusions 42 of the locking plate 40 will then be positioned over the ends of the bone screws 16, preventing the screws 16 from backing out.

The interbody fusion device of the present invention can be made from any desired materials. In one example, the load bearing device is made from PEEK® (or a similar material), bone, metal, or any other structural substitute. If the components of the interbody fusion device are radio lucent (such as with PEEK®), then doctors will be able to monitor the fusion process better with X rays. If desired, one or more radio opaque markers can be embedded into the interbody fusion device, which will show up in an X ray. Since the positions of the markers are known relative to the fusion device, a doctor can determine the position of the fusion device in an X ray by viewing the positions of the markers.

PEEK relative to titanium, is often the desired material to support the load between two vertebral bodies. This is because PEEK more closely mimics the stiffness of bone, whereas a titanium support is much stiffer than bone and is known to cause osteolysis.

A second school of thought is that the use of donor bone is the very best load bearing material available. However, at least one major problem with the use of bone is that it is only a spacer/cage. A bone ring is not strong enough to support or house bone screws, which are required to hold the vertebral bodies in place while fusion occurs. Therefore, a secondary device, such as an anterior plate and/or rods and pedicle screws must be used to create the necessary temporary fixation. Because of the closed geometry of a bone ring, any graft material must be loaded prior to implantation and not in-situ. As a result of these additional requirements, the use of a bone ring is not preferred by surgeons.

Understanding this, the retention device is designed to be shorter in height than the fusion bearing device. This design offers the strength of titanium to house the bone screws yet allows full loading only on the PEEK component.

An interbody fusion device of the present invention may be configured to any desired size or shape. In one example, load bearing devices can be provided in multiple thicknesses, allowing a surgeon to select a desired size (e.g., 8.0 mm, 10.0 mm, 12.0 mm, 14. mm, etc.). In the examples shown in the figures, the load bearing device has about 5° of lordosis. Of course any desired angle could be used.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising:
a fusion bearing device configured to fit between two adjacent vertebrae, the fusion bearing device having a top face and a bottom face through which an opening is formed that allows access to an interior space of the fusion bearing device to insert a fusion material;
a cantilevered shelf extending from an interior wall of the fusion bearing device into the interior space and past an inner edge of the top face, wherein the cantilevered shelf is disposed on a plane located between the top face and the bottom face;
a retention device configured to couple to the fusion bearing device; and
one or more bone screws coupled to the retention device to compress the two adjacent vertebrae to the fusion bearing the device.

2. The spinal fusion device of claim 1, wherein the fusion bearing device is substantially rectangular in shape.

3. The spinal fusion device of claim 1, further comprising an anti-backout mechanism coupled to the retention device.

4. The spinal fusion device of claim 3, further comprising a set screw configured to secure the anti-backout mechanism to the retention device, the set screw comprising a head that is configured to shear off.

5. The spinal fusion device of claim 1, wherein each of the one or more bone screws is configured to be inserted through an aperture formed in the retention device.

6. A spinal fusion device comprising:
a fusion bearing device configured to fit between two adjacent vertebrae, the fusion bearing device having a top face and a bottom face through which an opening is formed that allows access to an interior space of the fusion bearing device to insert a fusion material;
a cantilevered shelf extending from an interior wall of the fusion bearing device into the interior space and past an inner edge of the top face, wherein the cantilevered shelf is disposed on a plane located between the top face and the bottom face;
a window disposed in a side of the fusion bearing device to allow in-situ vertebral face preparation and in-situ graft delivery;
a retention device configured to couple to the fusion bearing device; and
wherein a border of the window and an outer border of the retention device complement one another so that the retention device can be placed into the window.

7. The spinal fusion device of claim 6, further comprising one or more fasteners configured to be coupled to the retention device to compress the two adjacent vertebrae to the fusion bearing the device.

8. The spinal fusion device of claim 7, wherein the one or more fasteners are bone screws.

9. The spinal fusion device of claim 7, wherein each of the one or more fasteners is configured to be inserted through an aperture formed in the retention device.

10. The spinal fusion device of claim 6, further comprising an anti-backout mechanism coupled to the retention device.

11. The spinal fusion device of claim 6, wherein the window is positioned on an anterior side of the fusion bearing device.

12. A spinal fusion device comprising:
a fusion bearing device having a shape of a ring that is configured to fit between two adjacent vertebrae, the fusion bearing device comprising:
a top face and a bottom face through which an opening is formed to allow access to end plates of the two adjacent vertebrae and wherein the top face and the bottom face include an inner edge defined by the opening that passes therethrough;
a window disposed in a side of the fusion bearing device to allow in-situ vertebral face preparation and in-situ graft delivery; and
a shelf extending from an interior wall of the fusion bearing device into the opening and past the inner edge of the top face, the shelf comprising a planar portion that extends across a width of the spinal fusion device, wherein the shelf comprises a single exposed edge that faces the window;
a retention device that is adapted to couple to the fusion bearing device;
one or more fasteners coupled to the retention device; and
wherein a border of the window and an outer border of the retention device complement one another so that the retention device can be placed into the window.

13. The spinal fusion device of claim 12, wherein the fusion bearing device is substantially rectangular shaped.

14. The spinal fusion device of claim 12, further comprising an anti-backout mechanism coupled to the retention device.

15. The spinal fusion device of claim 12, wherein the one or more fasteners are bone screws.

16. The spinal fusion device of claim 12, wherein each of the one or more fasteners is configured to be inserted through an aperture formed in the retention device.

17. The spinal fusion device of claim 12, wherein the opening in the fusion bearing device is adapted for receiving a fusion enhancing material.

18. The spinal fusion device of claim 12, wherein the window is positioned on an anterior side of the fusion bearing device.

19. The spinal fusion device of claim 12, wherein the fusion bearing device comprises allograft bone and the retention device comprises titanium.

20. The spinal fusion device of claim 14, further comprising a set screw configured to secure the anti-backout mechanism to the retention device, the set screw comprising a head that is configured to shear off.

* * * * *